United States Patent
Chavez et al.

(10) Patent No.: US 9,316,573 B2
(45) Date of Patent: Apr. 19, 2016

(54) NON-METALLIC DEBRIS MONITORING SYSTEM

(71) Applicant: BELL HELICOPTER TEXTRON INC., Fort Worth, TX (US)

(72) Inventors: Andrea Chavez, Colleyville, TX (US); Ryan Ehinger, Southlake, TX (US); Joseph Gerardi, Dryden, NY (US); Monte McGlaun, Abilene, TX (US); Eric Olson, Fort Worth, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 188 days.

(21) Appl. No.: 14/187,409

(22) Filed: Feb. 24, 2014

(65) Prior Publication Data

US 2015/0241328 A1    Aug. 27, 2015

(51) Int. Cl.
| | | |
|---|---|---|
| *G01N 21/00* | (2006.01) | |
| *G01N 15/06* | (2006.01) | |
| *G01N 29/02* | (2006.01) | |
| *B01D 21/24* | (2006.01) | |
| *B01D 21/26* | (2006.01) | |
| *G01N 33/28* | (2006.01) | |
| *G01N 1/22* | (2006.01) | |
| *G01N 15/00* | (2006.01) | |
| *G01N 15/02* | (2006.01) | |

(52) U.S. Cl.
CPC ............ *G01N 15/06* (2013.01); *B01D 21/2494* (2013.01); *B01D 21/265* (2013.01); *G01N 1/2202* (2013.01); *G01N 29/02* (2013.01); *G01N 33/2835* (2013.01); *G01N 15/0255* (2013.01); *G01N 2015/0011* (2013.01); *G01N 2015/0053* (2013.01)

(58) Field of Classification Search
CPC .......... G01N 29/036; G01N 2001/223; G01N 29/24; G01N 1/24
USPC .......................... 73/24.03, 28.01, 24.01, 23.2
See application file for complete search history.

(56) References Cited

U.S. PATENT DOCUMENTS

| | | | | |
|---|---|---|---|---|
| 5,026,318 A | * | 6/1991 | Jahnke | A22C 25/147 452/116 |
| 5,028,318 A | | 7/1991 | Aslin | |
| 5,403,473 A | * | 4/1995 | Moorehead | B01F 3/04 210/198.1 |
| 5,570,744 A | * | 11/1996 | Weingarten | B01D 17/00 166/357 |

(Continued)

FOREIGN PATENT DOCUMENTS

| | | | | |
|---|---|---|---|---|
| EP | 0716869 | * | 6/1996 | ......... G01N 15/1404 |
| EP | 0716869 A2 | | 6/1996 | |
| WO | 2014205832 A1 | | 12/2014 | |

OTHER PUBLICATIONS

Extended European Search Report dated Nov. 11, 2014 from counterpart EP App. No. 14162441.1.

(Continued)

*Primary Examiner* — Lisa Caputo
*Assistant Examiner* — Nigel Plumb
(74) *Attorney, Agent, or Firm* — James E. Walton

(57) ABSTRACT

A system and method to detect particles in a fluid stream. The system includes a separator configured to separate particles from bubbles passing through the fluid stream and a sensor configured to detect the particles. The method includes passing the fluid stream through the separator, separating the particles from bubbles passing through the fluid stream, and detecting the presence of the particles.

15 Claims, 3 Drawing Sheets

(56) References Cited

U.S. PATENT DOCUMENTS

| | | | | |
|---|---|---|---|---|
| 6,348,087 B1* | 2/2002 | Aslin | ................. | B04C 5/14 |
| | | | | 96/210 |
| 7,288,139 B1* | 10/2007 | Showalter | ......... | B01D 21/0009 |
| | | | | 210/167.03 |
| 2009/0211379 A1* | 8/2009 | Reintjes | ................. | G01N 1/14 |
| | | | | 73/863.23 |

OTHER PUBLICATIONS

Office Action dated Feb. 10, 2015 from counterpart EP App. No. 14162441.1.

Examination Report dated Aug. 5, 2015 from counterpart EP App. No. 14162441.1.

* cited by examiner

NON-METALLIC DEBRIS MONITORING SYSTEM

GOVERNMENT LICENSE RIGHTS

The U.S. Government has a paid-up license in this invention and the right in limited circumstances to require the patent owner to license others on reasonable terms as provided for by the terms of FARDS Program Contract No. W911 W6-10-2-0007.

BACKGROUND

1. Field of the Invention

The present application relates generally to debris detection systems, and more specifically, to a system configured to detect non-ferrous debris in a fluid stream.

2. Description of Related Art

Particles or contaminants in engine and gearbox lubricants pose an ongoing maintenance challenge and can be indicators of a developing problem. Monitoring particles in engine and gearbox lubricants can provide diagnostic and prognostic information that could result in a reduction in maintenance cost and the prevention of additional damage.

Current rotorcraft use magnetic chip detectors in order to monitor for potential component failure. With the advent of light weight, non-metallic components, such as ceramic bearings, the need arises to monitor the health of these components within the lubrication system.

Although the foregoing developments in the field of debris detectors represent great strides, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
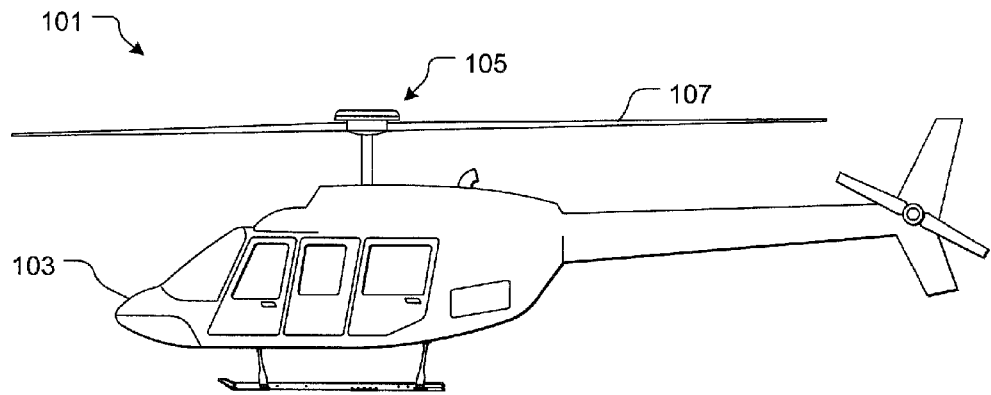
FIG. 1 is a side view of a helicopter according to a preferred embodiment of the present application.

While the system and method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the apparatus and method are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system of the present application overcomes the abovementioned problems commonly associated with conventional debris detection systems. Specifically, the system of the present application includes a conduit configured to separate particles from the gaseous fluid, and then monitor the accumulation of particles, if any, within the stream of fluid with a monitoring system. Further detailed description of these features are provided below and illustrated in the accompanying drawings.

The system and method of the present application will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Referring now to the drawings wherein like reference characters identify corresponding or similar elements throughout the several views, FIG. 1 depicts an aircraft 101 in accordance with a preferred embodiment of the present application. In the exemplary embodiment, aircraft 101 is a helicopter having a fuselage 103 and a rotor system 105 carried thereon. A plurality of rotor blades 107 is operably associated with rotor system 105 for creating flight.

Figure 2:
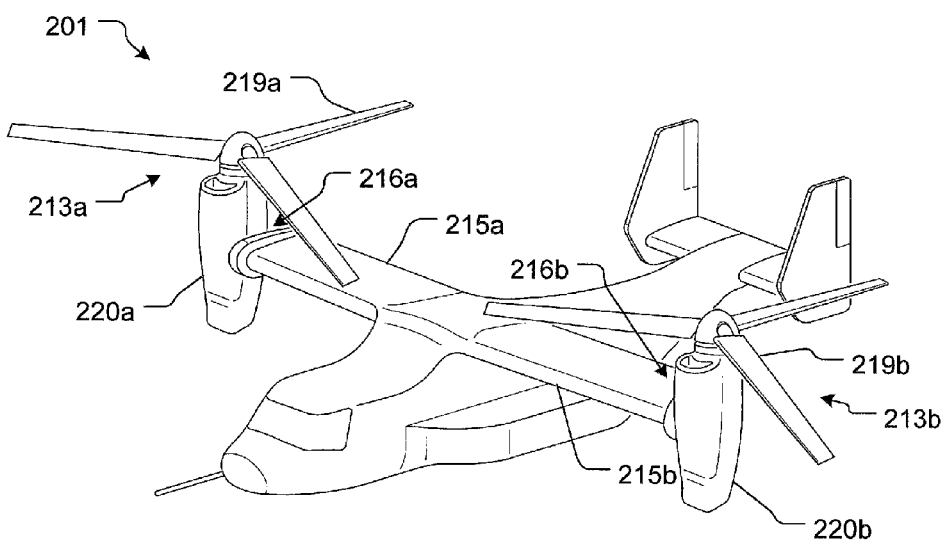
FIG. 2 is a perspective view of a tiltrotor aircraft according to an alternative embodiment of the present application.

Although shown associated with a helicopter, it will be appreciated that the system of the present application could also be utilized with different types of rotary aircraft and vehicles. For example, FIG. 2 illustrates a tiltrotor aircraft 201 that utilizes the system in accordance with the present application.

Tiltrotor aircraft 201 includes rotor assemblies 213a and 213b that are carried by wings 215a and 215b, and are disposed at end portions 216a and 216b of wings 215a and 215b, respectively. Tilt rotor assemblies 213a and 213b include nacelles 220a and 220b, which carry the engines and transmissions of tilt rotor aircraft 201, as well as, rotor proprotors 219a and 219b on forward ends 221a and 221b of tilt rotor assemblies 213a and 213b, respectively. Tilt rotor assemblies 213a and 213b move or rotate relative to wing members 215a and 215b between a helicopter mode in which tilt rotor assemblies 213a and 213b are tilted upward, such that tilt rotor aircraft 201 flies like a conventional helicopter; and an airplane mode in which tilt rotor assemblies 213a and 213b are tilted forward, such that tilt rotor aircraft 201 flies like a conventional propeller driven aircraft.

Figure 3:
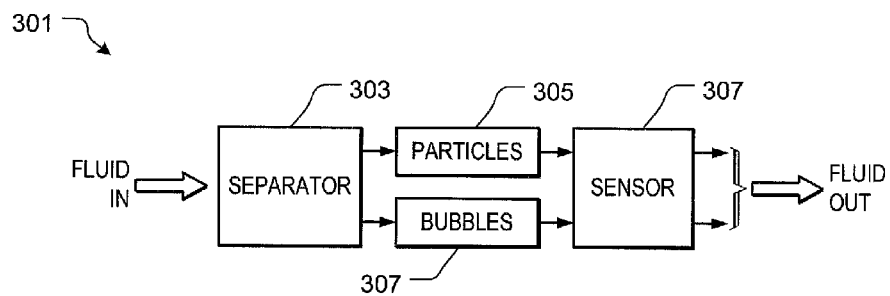
FIG. 3 is a simplified schematic of the debris detection system in accordance with a preferred embodiment of the present application.

FIG. 3 shows a simplified schematic of the debris detection system 301 in accordance with a preferred embodiment of the present application. In the contemplated embodiment, system 301 receives fluid through a separator 303 configured to separate particles and/or particles from the bubbles, as indicated by boxes 305, 307. Thereafter, a monitoring system utilizes a sensor 307 to monitor the whether particles are present in the fluid stream.

In the contemplated embodiment, as will be discussed more fully below, the separator 303 uses a coil to create a centrifugal force on the fluid stream, which in turn forces the heavier particles to the outer periphery of inner area of the coils. Such features may also be achieved with a device having a cylindrical or conical shape in alternative embodiments. It will be appreciate that in some applications, it may be possible to achieve a significantly reduced flow speed to allow gravity to separate the particles from the bubbles.

One unique feature believed characteristic of the present application is separating the particles from the bubble prior to utilizing a monitoring system. It should be understood that bubbles are constantly present in the fluid stream due use of the fluid. For example, a lubrication system utilizes a lubricant that is constantly in gaseous communication with air during the lubrication process, which in turn forms bubbles in the fluid stream. It should also be understood that it is difficult, if not impossible, to distinguish between bubbles and particles when intermixed with each other. Thus, there is a need to separate the bubbles and particle prior to utilizing the sensor 307.

Figure 4:
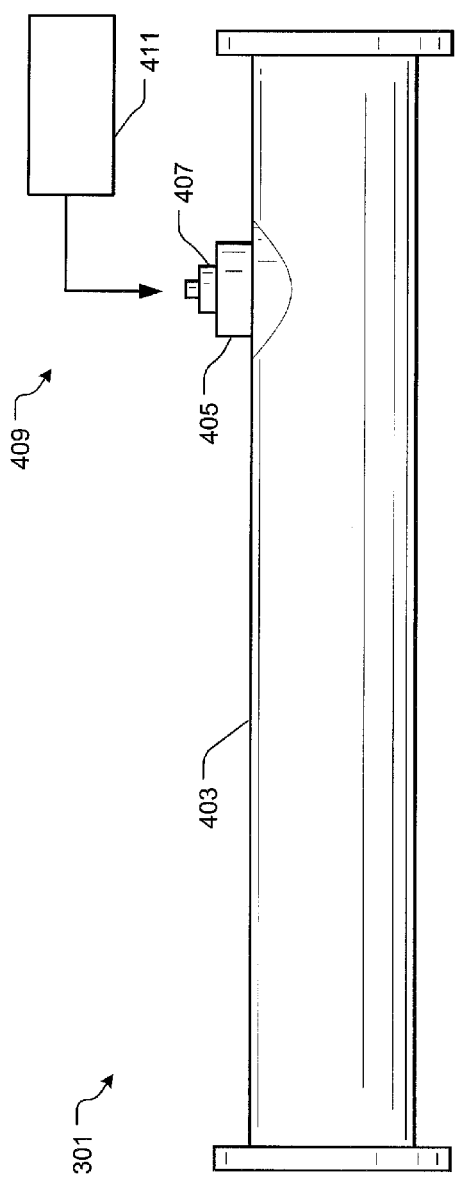
FIG. 4 is a front view of the debris detection system in accordance with the preferred embodiment of the present application.
Figure 5:
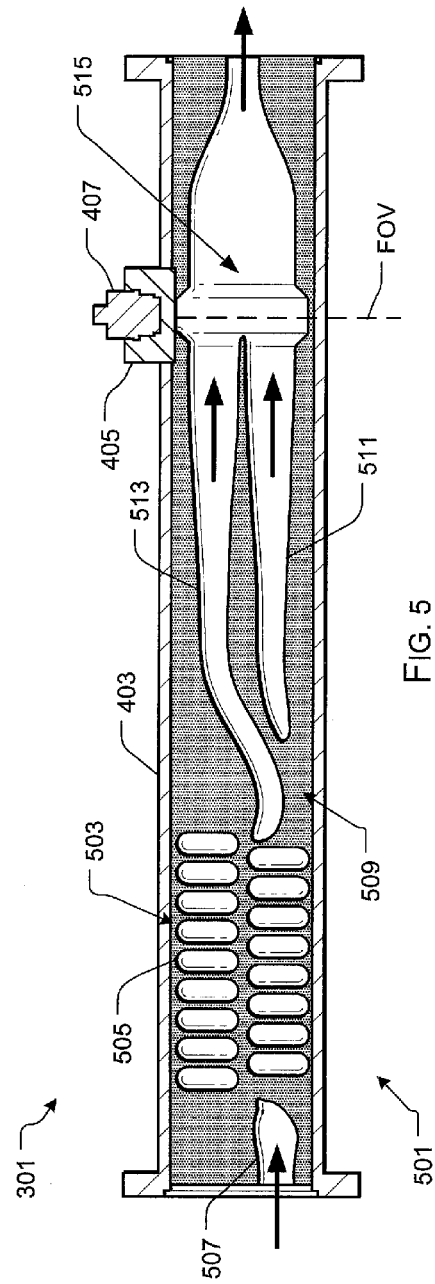
FIG. 5 is a front cross-sectional view of the debris detection system of FIG. 4.

In FIGS. 4 and 5, respective side and longitudinal cross-sectional views of system 301 are shown. In the exemplary embodiment, system 301 includes an elongated cylindrical body 401 and an integral housing 405, which in turn receives a sensor 407 configured to detect particles in the fluid stream.

A monitoring system 409 is shown operably associated with sensor 407 and is configured to monitor particles passing through the fluid stream. The monitoring system 409 is also configured to provide either visual or audio indication when contaminants are present. To achieve this feature, monitoring system 409 could include a computer 411 with a display in communication with sensor 407. For the sake of simplicity, the components of computer 411 and associated devices are not discussed herein for such features are commonly known in the art.

Figure 6:
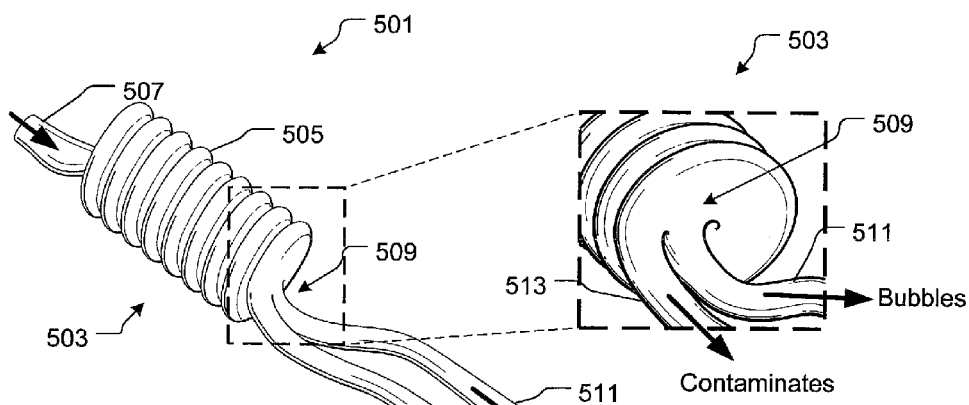
FIG. 6 is an oblique view of the conduit of the debris detection system of FIG. 4.
Figure 7:
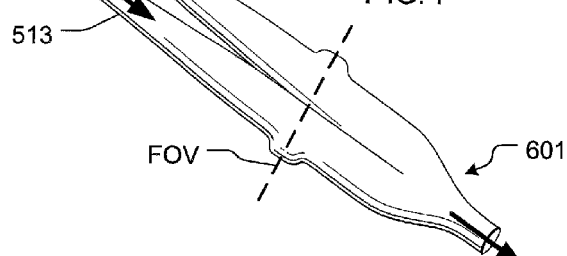
FIG. 7 is an enlarged oblique view of the flow separator of FIG. 6.

As depicted in FIGS. 5 and 6, system 301 includes one or more of a conduit 501 that extends through body 403 from a first end to an opposing second end. Conduit 501 is configured to channel the fluid through the various sections of system 301. Specifically, conduit 501 includes a separator 503 having a plurality of spiraling coils 505 in communication with an input fluid channel 507 and output section 509.

In the preferred embodiment, the fluid flow is continuous; however, it is also contemplated using segregation method, including batch methods, to divide out the particles from the fluid stream.

As discussed above, one unique feature believed characteristic of the present application is the process of separating the bubbles from particles. Thus, coils 505 are configured to cause a centrifugal force on the fluid, thereby separating the lighter density bubbles from the denser particles. In the preferred embodiment, coils are utilized; however, it is also contemplated utilizing any mechanically separated concept such as a spinning device configured to push out heavier particles radially.

After the fluid passes through the separator 503, the output section 509 bifurcates into two channels: a first channel 511 configured to channel the bubbles and a second channel 513 configured to channel particles. In the exemplary embodiment, channels 511, 513 increase in diameter as the fluid reaches the monitoring chamber 515 of conduit 501. However, it is also contemplated having channels that retain substantially the same diameter in alternative embodiments.

The next step includes the process of monitoring the fluid with the sensor 407. Thus, as the fluid enters the monitoring chamber 515, the sensor detects the presences of particles passing through the fluid stream at the sensor's field-of-view, as indicated by dashed line FOV. Because the bubbles are separated from particles, the sensor is capable of distinguishing between bubbles and particles.

Although shown with the bubbles being channeled near the sensor, it will be appreciated that this is a desire, but not a necessary feature, of the present application. Further, system 301 utilizes one FOV; however it is also contemplated using multiple FOVs and sensors in alternative embodiments.

In the preferred embodiment, sensor 407 is an acoustic sensor; however, it will be appreciated that alternative embodiments could utilize an optical, radio isotope, and other similarly suitable sensors that can detect the presence of particles, both metallic and non-metallic, in a fluid stream.

It will be appreciated that the sensor 407 could be any type of sensor that can detect particles in a fluid. In one embodiment, a sonic sensor is used that could detect size and axial position of particles. This feature allows the user to use a single sensor to look at both the air side and the particle side at the same time, and distinguish which was which by distance from the sensor. If a different type of sensor could not measure axial position, then the same thing could be accomplished by using one sensor on the particle side, and one on the air side.

It is apparent that a system and method with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system to detect particles in a fluid stream, comprising:
 a separator configured to separate particles from bubbles passing through the fluid stream, the separator having:
  a plurality of coils that form a first channel and a second channel;
 a sensor configured to detect the particles; and
 a monitoring chamber in fluid communication with both the first channel and the second channel;
 wherein the sensor is positioned such that a field of vision extends through the monitoring chamber.

2. The system of claim 1, further comprising:
 a monitoring system operably associated with the sensor and configured to monitor and provide indication of particles passing through the fluid stream.

3. The system of claim 1, wherein:
the coils are configured to separate the particles from the bubbles.

4. The system of claim 3, wherein:
the bubbles and fluid pass through the first channel and the particles and fluid passes through the second channel.

5. The system of claim 1, wherein the sensor is an acoustic sensor.

6. A method to detect particles in a fluid stream, comprising:
providing the system of claim 1;
passing the fluid stream through the separator;
separating the particles from bubbles passing through the fluid stream via a first channel and a second channel of the separator;
combining the fluid passing through the first channel and the second channel in a chamber; and
detecting the presence of the particles in the fluid stream passing through the chamber with a sensor.

7. The method of claim 6, wherein the step of separating the bubbles and particles is achieved through centrifugal force.

8. The method of claim 7, wherein the step of using centrifugal forces is achieved by passing the fluid stream through a plurality of coils of the conduit.

9. The method of claim 7, wherein the step of detecting the presence of particles is achieved with an acoustic sensor.

10. The method of claim 6, further comprising:
channeling the bubbles in the first channel; and
channeling the particles in the second channel.

11. A system, comprising:
a body;
a conduit disposed within and passing through the body, the conduit being configured to channel fluid through the body, the conduit having:
a separator configured to bifurcated into a first channel and a second channel;
a sensor held by the body and configured to sense particles passing through the fluid; and
a monitoring chamber in fluid communication with both the first channel and the second channel.

12. The system of claim 11, wherein the separator is a plurality of circular coils.

13. The system of claim 11, wherein the first channel is nearer to the sensor than the second channel.

14. The system of claim 11, wherein the body is cylindrical in shape.

15. The system of claim 11, wherein the sensor is an acoustical sensor.

* * * * *